United States Patent [19]

Easterbrook, III

[11] Patent Number: 5,575,758
[45] Date of Patent: Nov. 19, 1996

[54] LARYNGOSCOPE BLADE

[75] Inventor: William A. Easterbrook, III, Westwood, N.J.

[73] Assignee: Vital Signs, Inc., Totowa, N.J.

[21] Appl. No.: 323,549

[22] Filed: Oct. 17, 1994

[51] Int. Cl.$^6$ ........................................... A61B 1/26
[52] U.S. Cl. ........................... 600/193; 600/190; 600/199
[58] Field of Search .................................. 600/185, 187, 600/190, 193, 194, 199

[56] References Cited

U.S. PATENT DOCUMENTS

| | | | |
|---|---|---|---|
| 2,289,226 | 7/1942 | Van Foregger | 600/193 |
| 2,646,036 | 3/1950 | Allyn et al. | 600/193 |
| 3,598,113 | 8/1971 | Moore et al. | 600/185 |
| 3,856,001 | 12/1974 | Phillips | 600/194 |
| 3,943,920 | 3/1976 | Kandel | 600/190 |
| 4,337,761 | 7/1982 | Upsher | 128/11 |
| 4,406,280 | 9/1983 | Upsher | 128/11 |
| 4,437,458 | 3/1984 | Upsher | 128/11 |
| 4,517,964 | 5/1985 | Upsher | 128/11 |
| 4,527,553 | 7/1985 | Upsher | 128/11 |
| 4,546,762 | 10/1985 | Upsher | 128/11 |
| 4,557,256 | 12/1985 | Bauman | 128/11 |
| 4,570,614 | 2/1986 | Bauman | 128/11 |
| 4,573,451 | 3/1986 | Bauman | 128/11 |
| 4,579,108 | 4/1986 | Bauman | 128/10 |
| 4,583,528 | 4/1986 | Bauman | 128/11 |
| 4,592,343 | 6/1986 | Upsher | 128/11 |
| 4,596,239 | 6/1986 | Bauman | 128/11 |
| 4,607,623 | 8/1986 | Bauman | 128/11 |
| 4,669,449 | 6/1987 | Bauman | 128/11 |
| 4,679,547 | 7/1987 | Bauman | 128/10 |
| 4,729,367 | 3/1988 | Bauman | 128/11 |
| 4,815,451 | 3/1989 | Bauman | 128/11 |

OTHER PUBLICATIONS

North American Medical Products Inc 1985 Product Sheet for D. L. Scope System—1 page.
The Upsher Laryngoscope Corp. 1989 Product Sheet for Upsher Disposables–1 page.
Anesthesia Medical Specialties, undated, Product Sheet for "Latest Advances in Fiber–Optic Laryngoscopic Design"–1 page 2 sides.

*Primary Examiner*—Lynne A. Reichard
*Assistant Examiner*—Kelly McGlashen
*Attorney, Agent, or Firm*—R. Gale Rhodes, Jr.

[57] ABSTRACT

Improved plastic laryngoscope blade providing increased resistance to torsional deformation and for being coupled to a laryngoscope handle, the blade includes a plastic body including a generally curved spatula portion, a web portion extending outwardly from an edge portion of the spatula portion, and a flange portion extending inwardly from an outer portion of the web portion and residing at least partially over a portion of the spatula portion, and a coupling provided on an end of the spatula portion for coupling the blade to the handle.

3 Claims, 2 Drawing Sheets 5,575,758

1
LARYNGOSCOPE BLADE

BACKGROUND OF THE INVENTION

This invention relates generally to a new and improved laryngoscope blade for use in combination with a laryngoscope handle, and more particularly it relates to a new and improved laryngoscope blade having improved resistance against torsional deformation.

FIELD OF THE INVENTION

Laryngoscopes are well known to the art and generally comprise a laryngoscope blade and cooperating laryngoscope handle. Metal laryngoscope blades and metal handles are known to the art, and plastic laryngoscope blades are known to the art for use with cooperating laryngoscope handles.

An example of a prior art laryngoscope is disclosed in U.S. Pat. No. 4,570,614 patented Sep. 18, 1986, entitled LARYNGOSCOPE WITH DISPOSABLE BLADE AND LIGHT CONDUCTOR, Jack Bauman inventor; this patent is incorporated herein by reference as if fully reproduced herein and is referred to hereinafter as the "'614 patent." The '614 patent discloses a laryngoscope handle 10 and several different embodiments of a disposable, plastic laryngoscope blade such as blade 11 of FIGS. 1–2, 4 and 5, and blade 33 of FIG. 7 and blade 39 of FIG. 9. These laryngoscope blades, such as for example laryngoscope blade 11 of FIG. 2 of the '614 patent, include coupling means 14 for removably mounting the laryngoscope blade 11 to the battery filled handle 10 through the cooperative engagement of the laryngoscope blade coupling means 14 and handle pivot pin 21, FIG. 2 of the '614 patent, permitting the laryngoscope blade 11 to be positioned in a folded position substantially parallel to the handle 10 and into an operating or extended position substantially perpendicular to the handle 10 such as shown in FIG. 1 of the '614 patent.

As further known to those skilled in the art, plastic laryngoscope blades perform substantially the same function as the metal laryngoscope blades known to the art, however, at least some of the prior art plastic laryngoscope blades exhibit undesirable or unwanted torsional deformation upon the physician inserting the plastic laryngoscope blade into the airway of the patient and as he manipulates the plastic laryngoscope blade about as he inserts the endotracheal tube into the patient. Such torsional deformation can cause the physician to apply undesirable excessive force to the patient's tongue, laryngeal and pharyngeal tissues and can obscure the physician's view of the patient's vocal chords.

Accordingly, there is a need in the plastic laryngoscope blade art for an improved plastic laryngoscope blade which has improved or increased resistance to such torsional deformation.

SUMMARY OF THE INVENTION

It is the object of the present invention to satisfy the foregoing need in the art.

An improved laryngoscope blade embodying the present invention and satisfying such need may include a generally curved spatula portion, a web portion extending outwardly from an edge of the spatula portion, a flange portion extending inwardly from an outer edge of the web portion and residing at least partially over the spatula portion and a coupling provided on an end of the spatula portion for coupling the blade to the handle.

2
BRIEF DESCRIPTION OF THE DRAWINGS

DESCRIPTION OF THE PREFERRED EMBODIMENT

Figure 1:
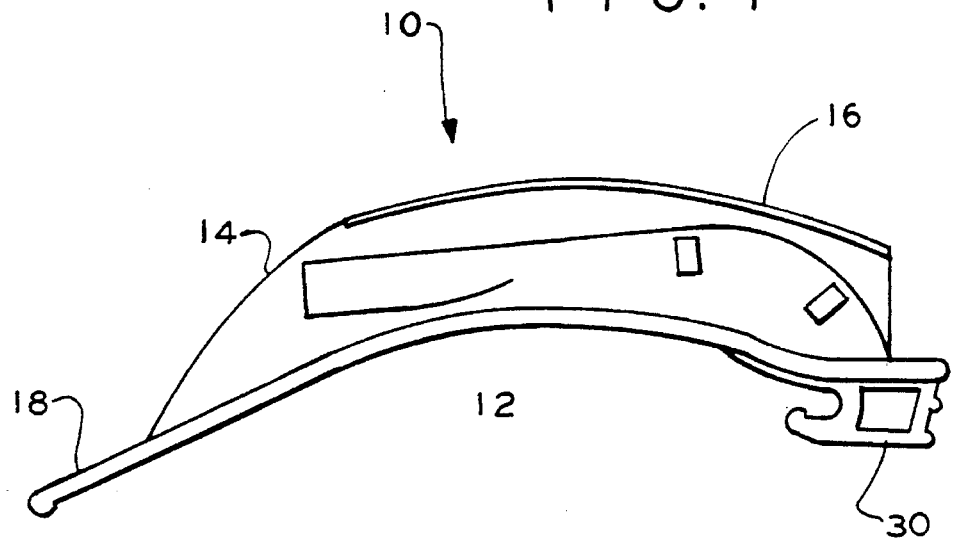
FIG. 1 is a side view of the improved laryngoscope blade of the present invention.

Referring now to the drawings, an improved laryngoscope blade embodying the present invention is indicated by general numerical designation 10. Blade 10 includes a body of plastic material, suitably formed such as by injection molding from a suitable plastic material, and includes integrally formed spatula portion 12, web portion 14, and flange portion 16.

Figure 3:
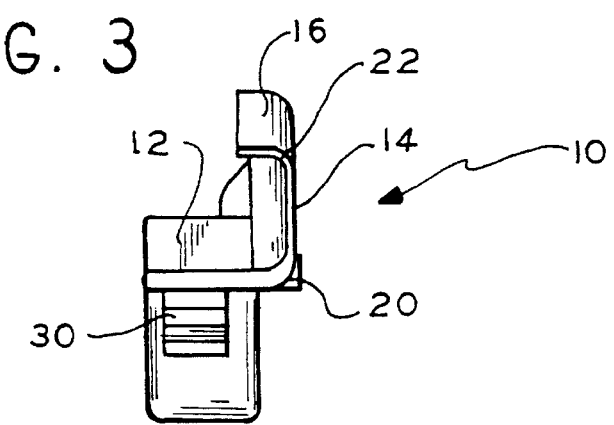
FIG. 3 is an end view of FIG. 1.
Figure 4:
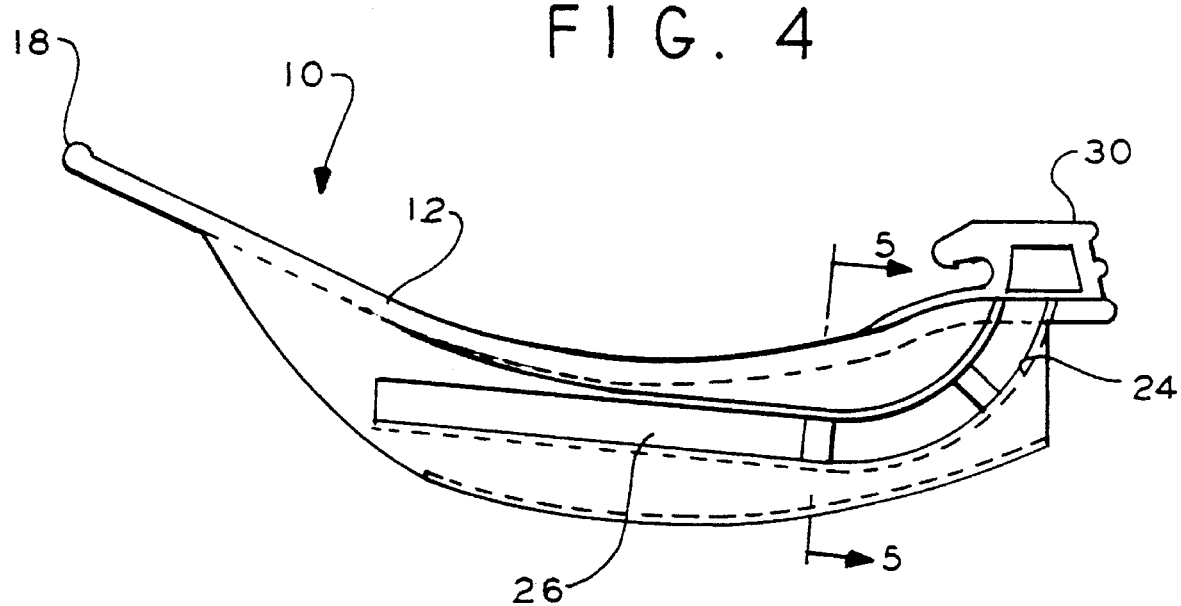
FIG. 4 is a side view of FIG. 1 opposite the side view shown in FIG. 1 but with the blade shown inverted with respect to FIG. 1.
Figure 5:
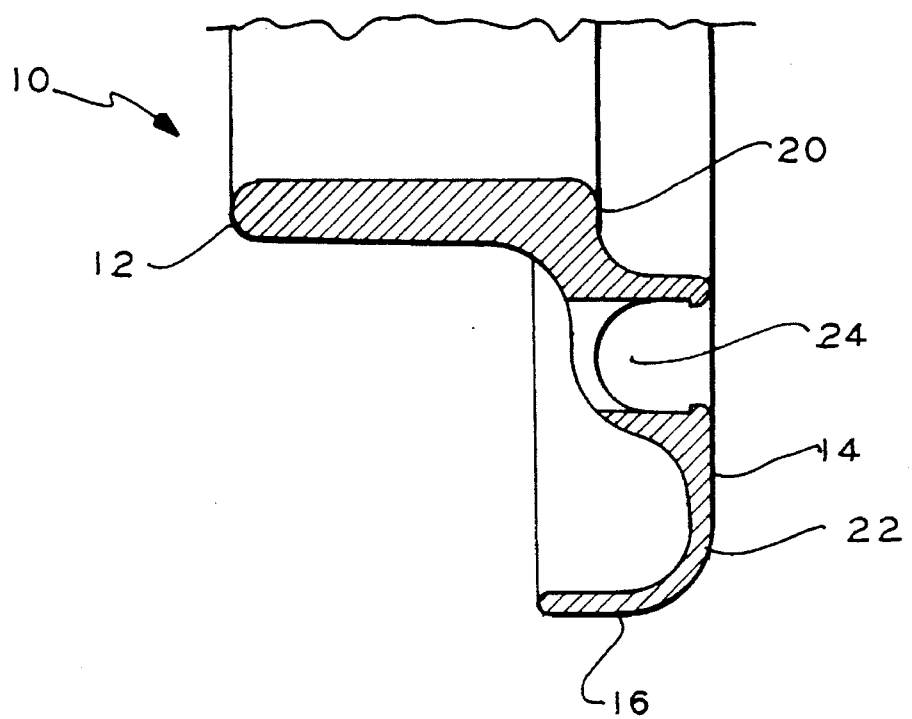
FIG. 5 is a cross-sectional view taken generally along the line 5—5 in FIG. 4 in the direction of the arrows.

The spatula portion 12, note FIGS. 1 and 4, is generally curved and may include a generally straight tip portion 18 and includes an edge portion 20, note FIGS. 3 and 5. It will be understood that the web portion 14, note particularly FIGS. 1, 3 and 4, extends perpendicularly and is offset from the edge portion 20 at least along a portion of the length thereof as may be noted particularly in FIGS. 1 and 4. The web portion 14, note FIGS. 3 and 5, includes an outer portion 22, and it will be noted particularly from FIGS. 3 and 5 that the flange portion 16 extends inwardly from the web portion 14 and generally perpendicular to and spaced from, at least a portion of, the spatula portion 12.

Figure 2:
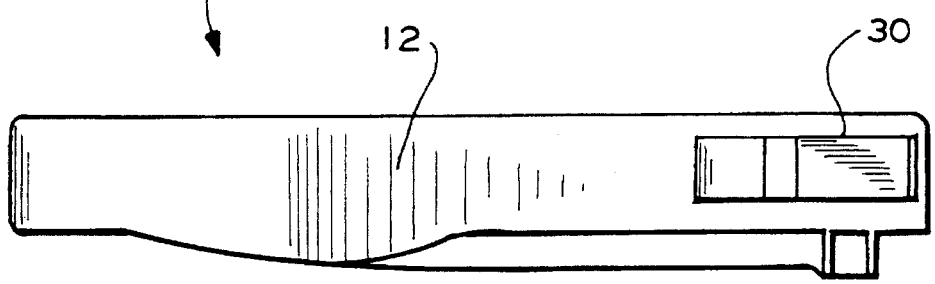
FIG. 2 is a bottom view of FIG. 1.

Referring particularly to FIGS. 4 and 5, it will be understood that the web portion 14 includes a generally semi-circular in cross section channel 24 for receiving a light conductor 26 (FIG. 4) which performs substantially the same function as the light conductor 15 shown in FIG. 2 of the '614 patent.

The blade 10 further includes integrally formed coupling means 30 formed generally at one end of the spatula portion 12. It will be understood that the coupling means 30 performs substantially the same function as the coupling means 14 of the laryngoscope blade 11 shown in FIG. 2 of the '614 patent and is for removably attaching the laryngoscope blade to a laryngoscope handle such as the handle 10 shown in the '614 patent.

It will be understood that the spatula portion 12 of the blade 10 of the present invention is for elevating the patient's tongue and that the flange 16 is for preventing the teeth of the patient from biting down on the light conductor 26. Such spatula portion and flange portion perform substantially the same function as the corresponding structure of the plastic laryngoscope blades shown and described in the '614 patent.

It has been discovered that by providing the improved laryngoscope blade 10 of the present invention with the structure and structural elements described above and shown in the drawings, the laryngoscope blade 10 has improved resistance to the torsional rotation noted above in the Background of the Invention.

The top, side and end designations referred to in the descriptions given to the FIGS. will be understood to be merely relative descriptions providing an understanding of the relative orientations of the structural elements shown in the drawings. It will be further understood, generally, that laryngoscope blades generally do not have such specific top, side and end views but are oriented in various positions as illustrated in FIG. 1 of the '614 patent.

It will be understood by those skilled in the art that many modifications and variations may be made in the present invention without departing from the spirit and the scope thereof.

What is claimed is:

1. An improved plastic laryngoscope blade providing increased resistance to torsional deformation, the blade for being coupled to a laryngoscope handle, comprising:

a plastic body including a generally curved spatula portion including an edge portion, a web portion including an outer portion and a flange portion extending inwardly from said web portion along said outer portion and residing at least partially over at least a portion of said spatula portion, and coupling means provided on said spatula portion for coupling said body to said handle; and said spatula portion including an upper surface, said edge portion defining an outer surface of the blade, and said web portion extending from said upper surface of said spatula portion such that said web portion extends from a position adjacent to said edge portion in a direction which is perpendicular to and offset from said upper surface of said spatula portion.

2. An improved plastic laryngoscope blade for being removably attached to a laryngoscope handle and which improved laryngoscope blade provides improved resistance to torsional deformation, comprising:

a body of plastic material including integrally formed spatula portion, web portion, flange portion and coupling portion;

said spatula portion including an upper surface and having a length and including at least a curved portion and a side edge portion defining an outer surface of the blade, said web portion extending from said upper surface of said spatula portion such that said web portion extends from a position adjacent to said side edge portion in a direction which is perpendicular to and offset from said upper surface of said spatula portion, said web portion including an outer portion, said flange portion extending inwardly and generally perpendicularly from said outer portion and generally parallel to and spaced from said spatula portion and residing at least partially over at least a portion of the length of said spatula portion.

3. The blade according to claim 2 wherein said web portion includes a channel for receiving a light guide and wherein said blade further comprises a light guide mounted in said channel.

* * * * *